(12) United States Patent
Efrati et al.

(10) Patent No.: US 11,207,046 B2
(45) Date of Patent: Dec. 28, 2021

(54) METHODS AND SYSTEMS FOR A MULTI-MODAL MEDICAL IMAGING SYSTEM

(71) Applicant: GE Precision Healthcare LLC, Milwaukee, WI (US)

(72) Inventors: Ken Efrati, Kiriat Motzkin (IL); Asaf Shtern, Moshav Betset (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 147 days.

(21) Appl. No.: 16/573,927

(22) Filed: Sep. 17, 2019

(65) Prior Publication Data

US 2021/0077053 A1 Mar. 18, 2021

(51) Int. Cl.
*G01N 23/02* (2006.01)
*A61B 6/00* (2006.01)
(Continued)

(52) U.S. Cl.
CPC .......... *A61B 6/5235* (2013.01); *A61B 6/032* (2013.01); *A61B 6/037* (2013.01); *A61B 6/0407* (2013.01); *A61B 6/4435* (2013.01); *A61B 6/544* (2013.01)

(58) Field of Classification Search
CPC ....... A61B 6/032; A61B 6/037; A61B 6/0407; A61B 6/4435; A61B 6/5235; A61B 6/544; A61B 6/4417; A61B 6/04; A61B 6/4258; A61B 6/0487; A61B 6/488; A61B 6/5276; A61B 6/584; A61B 5/055; A61B 6/03; A61B 6/0435; A61B 6/583; A61B 5/706; A61B 6/0428; A61B 6/0442; A61B 6/0492; A61B 6/56; A61B 17/00491; A61B 17/0057; A61B 17/12118; A61B 17/12181; A61B 17/3468; A61B 18/18; A61B 2017/00411; A61B 2017/0065; A61B 2017/00876; A61B 2017/1205; A61B 2090/367; A61B 2090/376; A61B 5/06; A61B 5/4504; A61B 5/4514; A61B 5/4528; A61B 6/508; A61B 90/36; A61B 6/507; A61B 5/0035; A61B 6/5247; A61B 5/415; A61B 5/418; A61B 6/501; A61B 6/502; A61B 6/548; A61B 6/4291; A61B 6/027;
(Continued)

(56) References Cited

U.S. PATENT DOCUMENTS 7,348,564 B2 3/2008 Wollenweber et al.
7,983,380 B2 7/2011 Guertin et al.
(Continued)

OTHER PUBLICATIONS

Osborne, D. et al., "Feasibility and Initial Performance of Simultaneous SPECT-CT Imaging Using a Commercial Multi-Modality Preclinical Imaging System," International Journal of Molecular Imaging, vol. 2015, No. 134768, Jun. 3, 2015, 11 pages.

*Primary Examiner* — Irakli Kiknadze
(74) *Attorney, Agent, or Firm* — McCoy Russell LLP (57) ABSTRACT

Various methods and systems are provided for multi-modal medical imaging systems. In one embodiment, a medical imaging system comprises a first gantry including a first bore and a second gantry including a second bore each adapted to receive a subject to be imaged by the medical imaging system, with the first bore having a first isocenter line and the second bore having a second isocenter line, where the first isocenter line and second isocenter line are offset from each other.

20 Claims, 6 Drawing Sheets

(51) Int. Cl.
*A61B 6/03* (2006.01)
*A61B 6/04* (2006.01)

(58) Field of Classification Search
CPC ..... A61B 6/4464; A61B 6/4447; A61B 6/481; A61B 6/486; A61B 6/503; A61B 6/504; A61B 6/5258; A61B 6/547; A61B 6/025; A61B 6/4035; A61B 6/482; A61B 6/5223; A61B 6/4405; A61B 6/541; A61B 90/39; A61B 2090/378; A61B 2090/3966; A61B 34/20; A61B 6/4441; A61B 6/4476; A61B 6/5205; A61G 2210/50; A61G 1/02; A61G 2200/14; A61G 7/103; A61G 15/02; G01T 1/2985; G01T 1/16; G01T 1/161; G01T 1/1615; G01T 1/166; G01T 1/2008; G01T 1/02; G01T 1/1611; G01T 1/1642; G01T 1/1603; G01T 1/2002; G01T 1/2018; G01T 1/1648; G01T 1/243; G01T 1/249; G01T 1/1612; G01T 1/1635; G01T 1/1644; G01T 1/366; G06K 7/10198; G01N 2223/419; G01N 23/046; G01N 21/763; G01N 2223/612; A61N 2005/1061; A61N 5/1049; A61N 5/1065; A61N 2005/1051; A61N 2005/1074; A61N 2005/1097; A61N 5/1037; A61N 5/1064; A61F 2/04; G21F 1/085; G21K 1/02; G06T 7/0012; G06T 11/006; G06T 7/20; G06T 2207/10116; G06T 2207/30004; G06T 2207/10081; G06T 2207/20048; G06T 2211/424; G06T 15/08; G06T 19/00; G06T 2207/10076; G06T 2207/10121; G06T 2207/10124; G06T 2207/30048; G06T 2207/30096; G06T 7/33; G06T 2207/10028
USPC ...................................... 378/4, 19, 62, 63, 20
See application file for complete search history.

(56) References Cited

U.S. PATENT DOCUMENTS

| | | | |
|---|---|---|---|
| 8,175,220 B2* | 5/2012 | Vaisburd | A61B 6/4441 378/63 |
| 8,630,696 B2* | 1/2014 | Kim | A61B 6/5235 600/427 |
| 8,977,026 B2* | 3/2015 | Bar-Shalev | G06T 7/74 382/131 |
| 9,014,330 B2* | 4/2015 | Takayama | A61B 6/54 378/19 |
| 9,192,346 B2* | 11/2015 | Zingerman | A61B 6/0487 |
| 9,433,388 B2 | 9/2016 | Noshi et al. | |
| 9,498,167 B2 | 11/2016 | Mostafavi et al. | |
| 9,974,494 B2 | 5/2018 | Mostafavi et al. | |
| 10,049,465 B2 | 8/2018 | Jain et al. | |
| 2007/0003021 A1 | 1/2007 | Guertin et al. | |
| 2011/0031323 A1 | 2/2011 | Nold et al. | |
| 2018/0000435 A1* | 1/2018 | Liu | A61B 6/032 |

* cited by examiner

METHODS AND SYSTEMS FOR A MULTI-MODAL MEDICAL IMAGING SYSTEM

FIELD

Embodiments of the subject matter disclosed herein relate to medical imaging, and more particularly, to medical imaging via multiple imaging modalities.

BACKGROUND

Combined imaging systems, such as combined computerized tomography (CT) and nuclear medicine (NM) imaging systems, are configured to scan objects in multiple modalities (e.g., CT and PET) and may be referred to as multi-modality or multi-modal imaging systems. Some multi-modal imaging systems include a gantry having multiple bores, and each bore may be configured for imaging in different modalities. Imaging a subject via a given modality may include positioning the subject within the respective bore configured to image in the given modality. Each modality may have a different field of view (FOV), with the FOV based in part on a configuration of the respective bore used for imaging.

In order to position the subject within the bores, the subject is often supported by a table configured to travel in an axial direction of the bores. A height of the table is adjustable to align the subject to be imaged with an isocenter line of a given bore, with detectors of the imaging system configured to rotate around the isocenter line and subject in order to image the subject. In some cases, it is advised to center the subject or a specific portion or organ of the subject against the isocenter line.

BRIEF DESCRIPTION

In one embodiment, a medical imaging system comprises a first gantry including a first bore and a second gantry including a second bore each adapted to receive a subject to be imaged by the medical imaging system, with the first bore having a first isocenter line and the second bore having a second isocenter line, where the first isocenter line and second isocenter line are offset from each other.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

The drawings illustrate specific aspects of the described multi-modal imaging system. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

Figure 3:
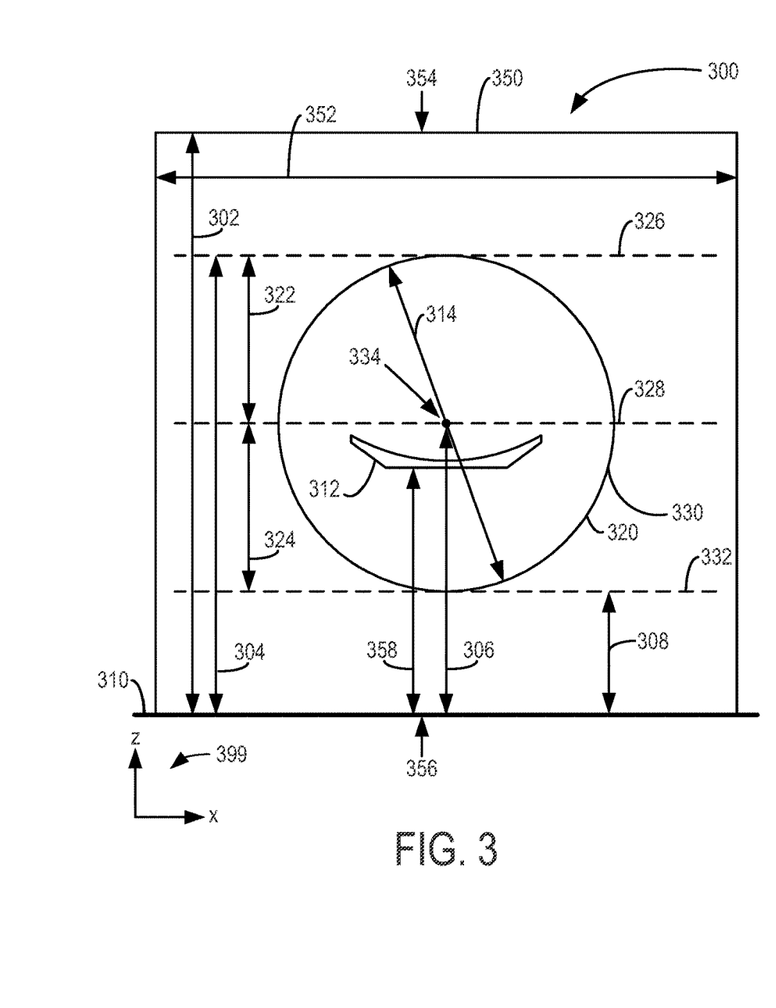
FIG. 3-4 show different views of a multi-modal imaging system including bores in an aligned configuration.
Figure 4:
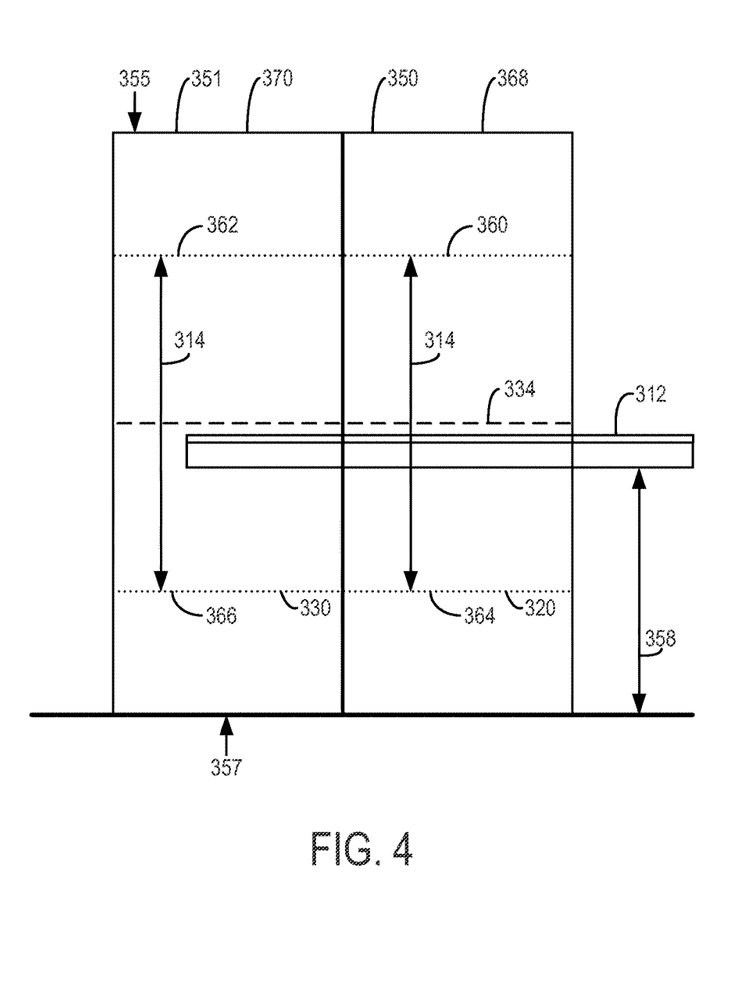

The following description relates to various embodiments of systems and methods for a multi-modal medical imaging system. A medical imaging system, such as the multi-modal imaging system shown by FIGS. 1-2, includes a housing having a plurality of bores. The multi-modal imaging system includes detectors and other components configured to image a subject via a plurality of different imaging modalities, and each given imaging modality may be associated with a respective bore of the plurality of bores. The multi-modal imaging system may image the subject via a first set of imaging modalities during conditions in which the subject is positioned within a first bore, and may image the subject via a second set of imaging modalities during conditions in which the subject is positioned within a second bore. Conventionally, the bores of a multi-modal imaging system are positioned in an aligned configuration in which an isocenter line of each bore is arranged coaxially with an isocenter line of each other bore, as shown by FIGS. 3-4.

Figure 5:
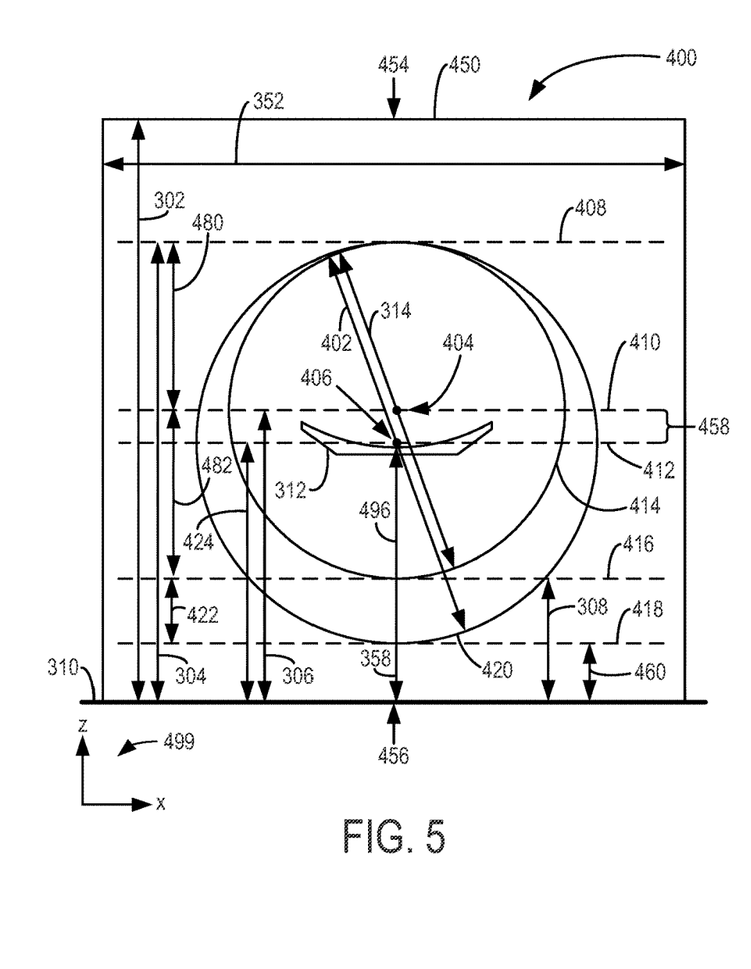
FIGS. 5-6 show different views of a multi-modal imaging system including bores in an offset configuration, according to an exemplary embodiment.
Figure 6:
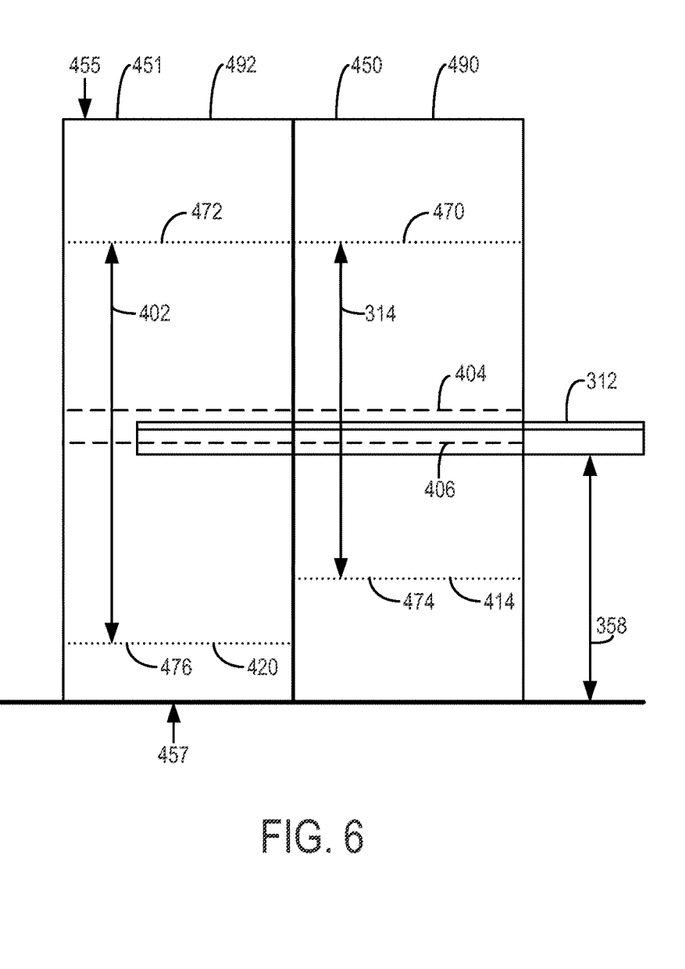

However, the multi-modal imaging system of the present disclosure includes first and second bores that are offset from each other (e.g., spaced apart from each other, and not coaxial with each other), as shown by FIGS. 5-6. The first and second bores are configured with different diameters and are positioned in a non-concentric arrangement such that the isocenter line of the first bore is offset from the isocenter line of the second bore. The subject may be positioned on an adjustable table including a portion configured to travel axially through the bores for imaging of the subject, according to the method shown by the flowchart of FIG. 7. By configuring the bores to be in the offset configuration, larger subjects may be imaged via the multi-modal imaging system while maintaining the size of the overall system/outer housing relative to systems that do not include bores in the offset configuration. Additionally, the FOV of each imaging modality may be appropriately sized relative to the subject to be imaged and not limited by the size of the bores, which may increase image quality.

For example, the first bore of the multi-modal imaging system may be configured for computerized tomography (CT) imaging with a first imaging FOV, and the second bore of the multi-modal imaging system may be configured for nuclear medicine (NM) imaging with a second imaging FOV, with the first FOV being smaller than the second FOV. During conditions in which larger subjects are scanned, the offset configuration of the bores may provide more of the subject to fit within the FOVs relative to systems in which the bores are in a non-offset configuration.

Further, by positioning the bores in the offset configuration described herein, an amount of vertical extension of the table supporting the subject may be reduced. For example, some tables may be configured to adjust to a maximum amount of vertical extension (e.g., a maximum table height). Offsetting the bores relative to each other such that the larger bore is positioned closer to the ground surface on which the outer housing sits may reduce an amount of vertical extension of the table in order to center the subject at the isocenter line of the larger bore. This configuration may enable tables having a smaller amount of vertical extension to be used for imaging of the subject via the multi-modal imaging system. In particular, although the multi-modal imaging system includes the larger sized bore, the lower, offset position of the larger sized bore enables the size of the housing to be maintained relative to systems that do not include offset bores while also maintaining compatibility with tables that have the same maximum height configuration used for imaging with systems that do not include offset bores.

As referred to herein, a multi-modal imaging system refers to a system configured to perform scans (e.g., imaging of a subject) in different modalities (e.g., CT, PET, etc.). A multi-modal imaging system may additionally be configured to perform scans in different modes (e.g., a fluoro mode and a tomosynthesis mode). Systems that are not configured to perform scans in different modalities, and which may or may not be configured to perform scans in different modes, may be referred to herein as uni-modal imaging systems.

The systems and methods are described herein with reference to the figures, and some elements having the same reference number in multiple figures may be described once and not re-introduced. The figures are intended to be illustrative rather than limiting and are included herewith to facilitate explanation of the systems and methods of the disclosure.

Figure 1:
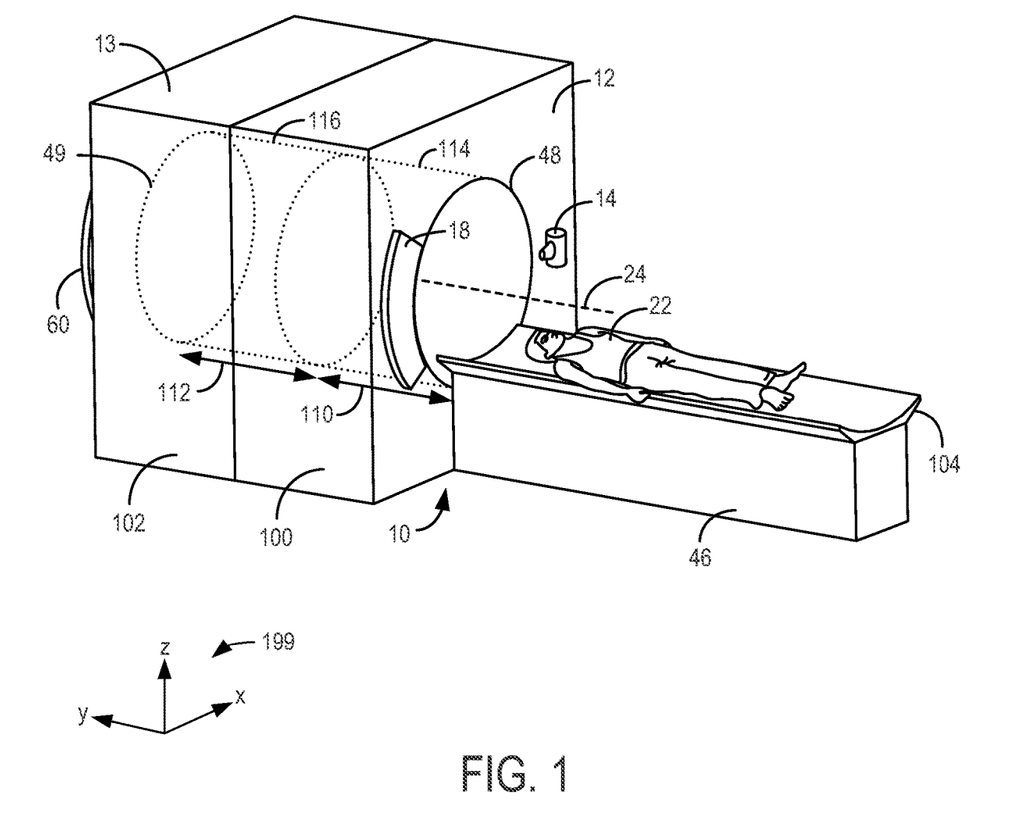
FIG. 1 shows a multi-modal imaging system, according to an exemplary embodiment.
Figure 2A:
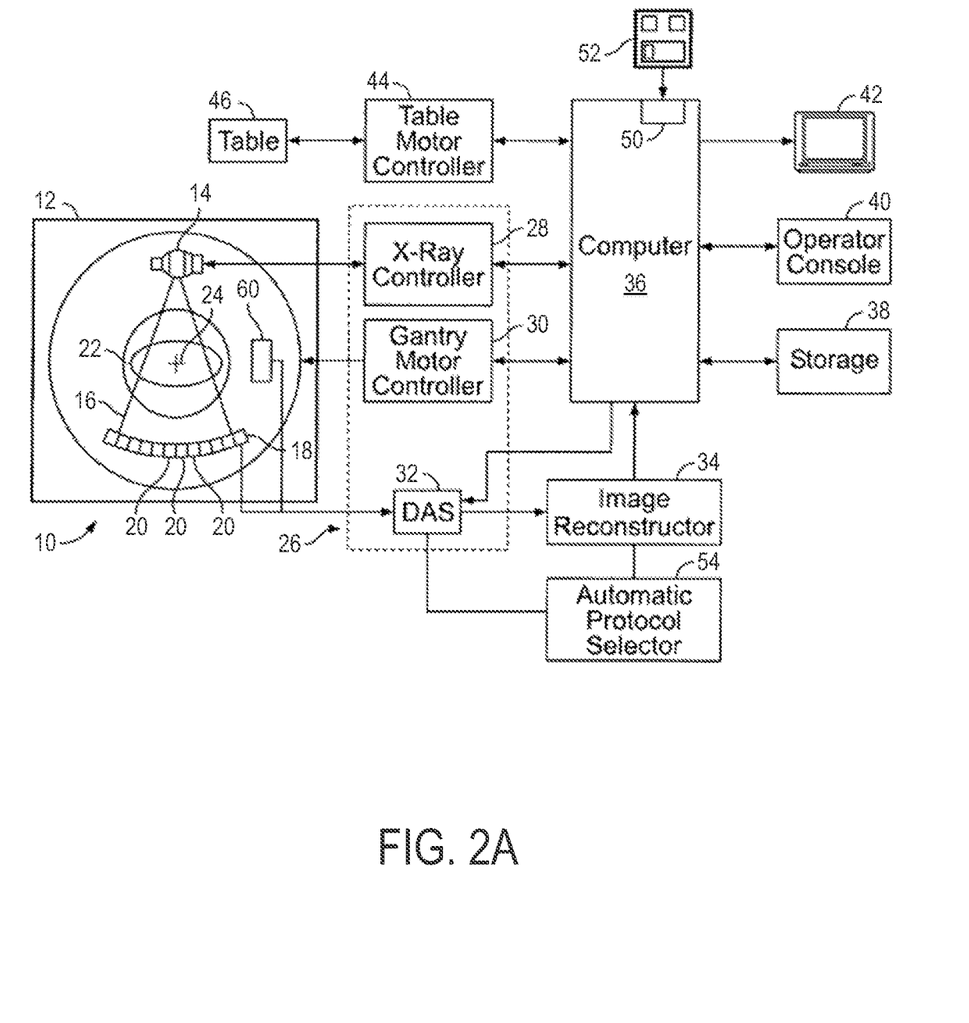
FIG. 2A schematically shows a block diagram a first modality unit of the multi-modal imaging system of FIG. 1, according to an exemplary embodiment.
Figure 2B:
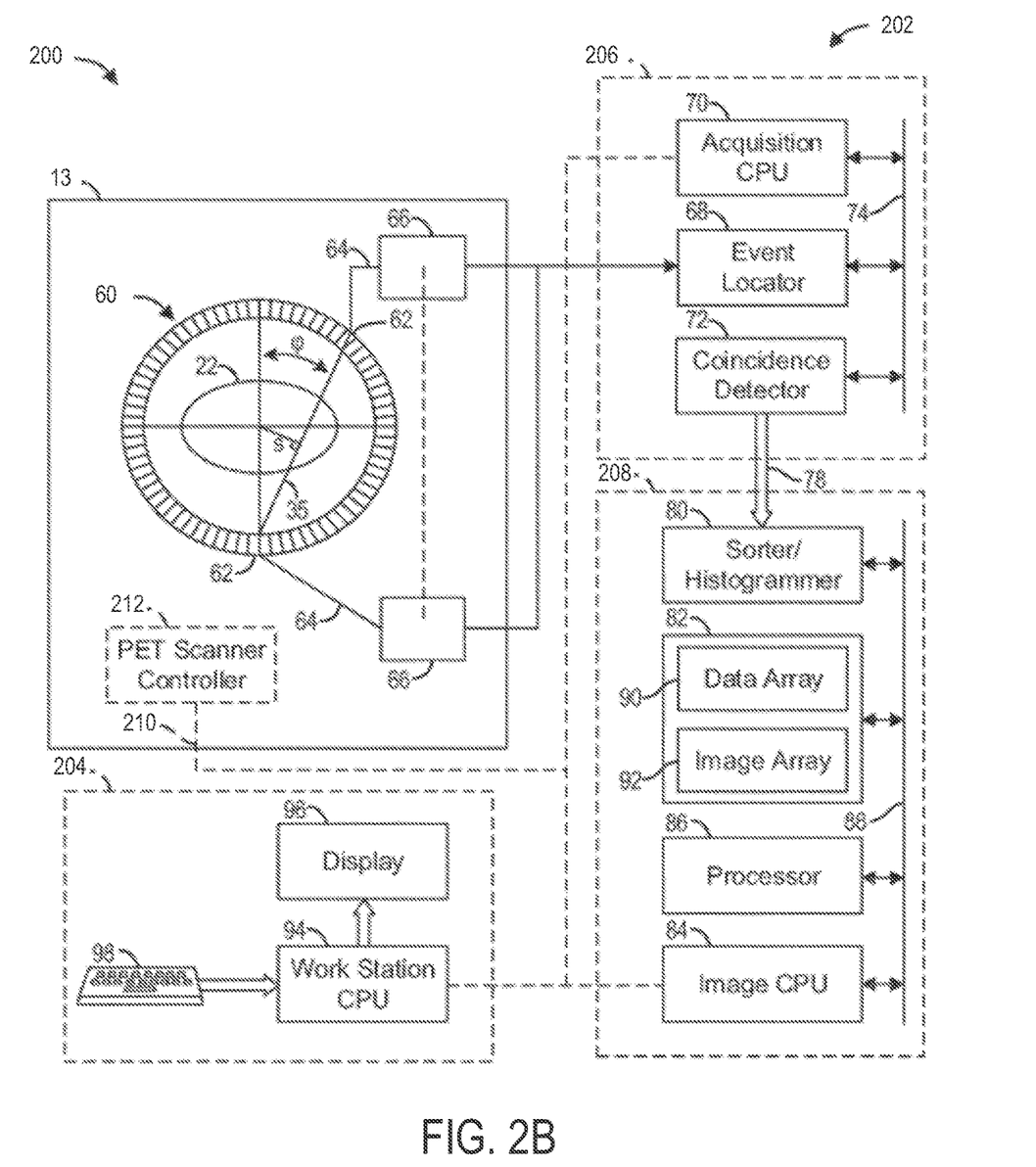
FIG. 2B schematically shows a block diagram a second modality unit of the multi-modal imaging system of FIG. 1, according to an exemplary embodiment.

Referring to FIGS. 1, 2A, and 2B, a multi-modal imaging system 10 is illustrated, and includes a first modality unit 100 and a second modality unit 102. In some embodiments, the first modality unit 100 is configured to provide imaging of a subject via at least a first imaging modality, and the second modality unit 102 is configured to provide imaging of the subject via at least a different, second imaging modality. The system 10 may scan a subject (e.g., an object, patient, etc.) in the first modality (e.g., CT) using the first modality unit 100 and/or scan the subject in the second modality (e.g., PET) using the second modality unit 102. In some embodiments, one or both of the first modality unit 100 and second modality unit 102 may be configured to scan the subject in multiple different modalities. For example, the second modality unit 102 may be configured to scan the subject via multiple NM imaging modalities such as PET, single-photon emission computed tomography (SPECT), etc. Optionally, modalities other than CT and NM are employed with system 10.

The first modality unit 100 includes gantry 12 and second modality unit 102 includes gantry 13. The first modality unit 100 is configured with a first signal source 14 (e.g., an X-ray source) at a first side that projects a beam of signals (e.g., X-rays) toward a detector array 18 on the opposite side of first modality unit 100 (e.g., the opposite side of gantry 12). Detector array 18 is formed by a plurality of detector rows that each include a plurality of detector elements 20 which together sense the projected signals that pass through a subject to be imaged, such as a medical patient 22. Each detector element 20 produces an electrical signal that represents the intensity of an impinging signal and hence allows estimation of the attenuation of the beam as it passes through the subject (e.g., patient 22). During a scan to acquire signal projection data, components of the first modality unit 100 (e.g., first signal source 14 and detector array 18) rotate about a center of rotation 24. FIG. 2 shows only a single row of detector elements 20 (e.g., a detector row). However, a multi-slice detector array 18 includes a plurality of parallel detector rows of detector elements 20 such that projection data corresponding to a plurality of slices can be acquired synchronously during a scan.

Second modality unit 102 includes a second detector 60 configured to receive signals projected through the body of the subject to be imaged by the second modality unit 102. For example, second detector 60 may be configured to receive radiation (e.g., gamma radiation) produced by a radiopharmaceutical introduced into the body of the subject to be imaged (e.g., during imaging via the PET imaging modality or other NM imaging modality). Second detector 60 is formed by a plurality of detector rows that each include a plurality of detector elements, which may be similar to detector elements 20. The detector elements sense signals projected through the body of the subject to be imaged, such as medical patient 22. Each detector element produces an electrical signal that represents the impinging signal and hence allows estimation of the origin of the signal passing through the subject. During a scan to acquire signal projection data, components of the second modality unit 102 (e.g., second detector 60) rotate about a center of rotation, which may be different from the center of rotation 24 during conditions in which bores of the multi-modal imaging system are in an offset configuration (as described further below). Second detector 60 may include a plurality of parallel detector rows of detector elements such that projection data corresponding to a plurality of slices can be acquired synchronously during a scan.

The multi-modal imaging system 10 includes multiple bores for imaging in the different modalities. The first modality unit 100 includes first bore 114 having first length 110 in the direction along center of rotation 24, and the second modality unit 102 includes second bore 116 having length 112 in the direction along center of rotation 24. In some embodiments, the first length 110 may be different from the second length 112 (e.g., a different amount of length). In other embodiments, first length 110 and second length 112 may be a same amount of length. First bore 114 is open at gantry opening 48, and second bore 116 is open at gantry opening 50. During imaging of the subject, table 46 may be adjusted in order to move the subject into the first bore 114 and/or second bore 116, as described further below.

Rotation of gantry 12 and the operation of signal source 14 are controlled by a control mechanism 26 of the multi-modal imaging system 10. Control mechanism 26 includes a signal controller 28 that provides power and timing signals to signal source 14, and a gantry motor controller 30 that controls the rotational speed and position of gantry 12. A data acquisition system (DAS) 32 in control mechanism 26 samples analog data from detector elements 20 and converts the data to digital signals for subsequent processing. An image re-constructor 34 receives the sampled and digitized signal data from DAS 32 and performs high-speed image reconstruction. The reconstructed image is applied as an input to a computer 36 which stores the image in a storage device 38. Computer 36 may include one or more processors, memory modules (e.g., transitory and/or non-transitory memory), etc. Computer 36 may receive commands and scanning parameters from an operator via console 40 that includes a user input device (e.g., a keyboard). An associated visual display unit 42 allows the operator to observe the reconstructed image and other data from the computer 36.

The operator supplied commands and parameters are used by computer 36 to provide control signals and information to DAS 32, signal controller 28, and gantry motor controller 30. In addition, computer 36 operates a table motor controller 44 which controls a motorized table 46 to position patient 22 in gantry 12. Particularly, table 46 moves at least a portion of patient 22 through gantry opening 48. The position of table 46 is adjustable in each of a vertical direction (e.g., the direction of the z-axis of reference axes 199) and an axial direction of the gantry 12 (e.g., the direction of the y-axis of reference axes 199). In some embodiments, the operator may adjust the position of the table 46 via the user input device of console 40 in electronic communication with computer 36. In other embodiments, the operator may adjust the position of the table 46 via a controller (e.g., control panel) directly coupled to the table 46. Adjusting the position of the table 46 may include raising or lowering the table 46 in the vertical direction and/or moving the table 46 into or out of the bores of the gantry 12 in the axial direction.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware on non-transitory memory of the computer 36. Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

The second modality unit 102 includes second detector 60 including a plurality of detector elements (shown in FIG. 2B and described below). In some embodiments, the detector array 18 of first modality unit 100 may be a CT detector array, with the second detector 60 and detector array 18 configured to detect different types of radiation (e.g., electromagnetic radiation). Each of second detector 60 and detector array 18 may be referred to herein as radiation detectors. Additionally, although described in a medical setting, it is contemplated that the benefits of the disclosure described herein may also accrue to other multi-modal imaging systems.

The detector array 18 has a plurality of rows (not shown) each having detector elements 20 which detect the X rays 16 passing through the patient 22. The intensity of the attenuated radiation beam 16 received at the detector array 18 is dependent upon the attenuation of a signal beam 16 by the patient 22. Each detector element 20 of the detector array 18 produces a separate electrical signal that is a measurement of the beam intensity at the detector location. The intensity measurements from all the detector elements 20 are acquired separately to produce a transmission profile.

In an exemplary embodiment, the signal source 14 and the detector array 18 are rotated with gantry 12 within the imaging plane and around the patient 22 to be imaged such that the angle at which the signal beam 16 intersects the patient 22 constantly changes. A group of signal attenuation measurements (e.g., projection data) from the detector array 18 at one gantry angle is referred to as a "view". A "scan" of the patient 22 comprises a set of views made at different gantry angles, or view angles, during one revolution of the signal source 14 and detector array 18. In an axial scan, the projection data is processed to construct an image that corresponds to a two-dimensional slice taken through the patient 22. One method for reconstructing an image from a set of projection data may be referred to as the filtered back projection technique. This process converts the integral attenuation measurements into an image representing attenuation of the patient in each pixel. The attenuation measurements may be converted into units of CT numbers or Hounsfield units in some embodiments.

During some conditions, a helical scan may be performed (e.g., to reduce scan time). To perform a helical scan, the patient 22 is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to the filtered back projection process, the data is weighted according to a helical weighing factor, which is a function of both the gantry angle and detector angle. The weighted data is then processed to generate CT numbers and to construct an image that corresponds to a two dimensional slice taken through the patient 22.

During operation of the multi-modal imaging system 10, multiple projections may be acquired synchronously with multiple detector rows. Similar to the case of helical scan, weighting functions may be applied to the projection data prior to the filtered back projection process.

As described above, the second modality unit 102 of multi-modal imaging system 10 may be configured to perform scans of the patient 22 via the PET imaging modality. During a PET scan, positrons (e.g., positively charged electrons or anti-electrons) are emitted by radionuclides that have been prepared using a cyclotron or other device. The radionuclides most often employed in diagnostic imaging are fluorine-18 (18F), carbon-11 (11C), nitrogen-13 (13N), and oxygen-15 (15O). Radionuclides are employed as radioactive tracers called "radiopharmaceuticals" by incorporating them into substances such as glucose or carbon dioxide.

The radiopharmaceutical may be injected into the patient (e.g., patient 22), where the radiopharmaceutical accumulates in an organ, vessel or the like, which is to be imaged. Specific radiopharmaceuticals may become concentrated within certain organs or, in the case of a vessel, specific radiopharmaceuticals may not be absorbed by a vessel wall. The process of concentrating often involves processes such as glucose metabolism, fatty acid metabolism, and protein synthesis.

After the radiopharmaceutical becomes concentrated within the organ of interest and while the radionuclides decay, the radionuclides emit positrons. The positrons travel a very short distance before they encounter an electron and, when the positron encounters an electron, the positron is annihilated and converted into two photons. This annihilation event is characterized by two features which are pertinent to imaging and particularly to medical imaging using the PET imaging modality. First, each annihilation photon has an energy of approximately 511 keV upon annihilation. Second, the two annihilation photons are directed in substantially opposite directions.

In PET imaging, if the general locations of annihilations can be identified in three dimensions, a three dimensional image of an organ of interest can be reconstructed for observation. To detect annihilation locations, a PET camera is employed (such as second detector 60). In some embodiments, the second detector 60 may include a PET camera. An exemplary PET camera includes a plurality of detectors and a processor which, among other things, includes coincidence detection circuitry.

The coincidence circuitry (not shown) identifies essentially synchronous pulse pairs which correspond to detectors which are essentially on opposite sides of the imaging area. Thus, a synchronous pulse pair indicates that an annihilation event has occurred on a straight line between an associated pair of detectors. Over an acquisition period of a few minutes, millions of annihilations are recorded, and each annihilation is associated with a particular detector pair via DAS 32 or another computing device (as discussed below), for example. After an acquisition period, recorded annihilation data can be used via any of several different well-known back projection procedures to construct the three dimensional image of the organ of interest.

During conditions in which the patient 22 is imaged via multiple imaging modalities, the patient 22 may be moved through each of the bores (e.g., first bore 114 and/or second bore 116) via adjustment of the axial position of table 46. For example, the patient 22 may be supported by the table 46 at an upper portion 104 of the table 46, and the upper portion 104 may move in the axial direction through the bores. Imaging the patient 22 via multiple imaging modalities may include first imaging the patient 22 via the first imaging modality while the patient 22 is positioned within the bore of the first modality unit 100, and then imaging the patient 22 while the patient 22 is positioned within the bore of the second modality unit 102. As another example, the patient 22 may first be imaged via the second imaging modality while the patient is positioned within the bore of the second modality unit 102, and then imaged via the first imaging modality while the patient is positioned within the bore of the first modality unit 100. Moving the patient 22 from the bore of the first modality unit to the bore of the second modality unit (or vice versa) may include adjusting both of the axial position of the upper portion 104 of the table 46 and the vertical position of the upper portion 104 of the table 46. For example, during imaging of the patient via the first modality unit 100, the vertical position of the table 46 may be different than the vertical position of the table 46 during imaging of the patient 22 via the second modality unit 102. In each example, the vertical position of the table 46 may be adjusted such that the patient 22 is located at the isocenter line of the respective bore during imaging (e.g., the bore of the first modality unit 100 during imaging via the first modality, or the bore of the second modality unit 102 during imaging via the second modality).

FIG. 2B is a block schematic diagram of a PET imaging system 200, which may be an example of the second modality unit 102 illustrated in FIG. 1, in accordance with an embodiment of the present disclosure. The PET imaging system 200 includes a detector ring assembly 60 including a plurality of detector crystals. The PET imaging system 200 also includes a controller or processor 202, to control normalization, image reconstruction processes, and perform calibration. Controller 202 is coupled to an operator workstation 204. Controller 44 includes a data acquisition processor 206 and an image reconstruction processor 208, which are interconnected via a communication link 210. PET imaging system 200 acquires scan data and transmits the data to data acquisition processor 206. The scanning operation is controlled from the operator workstation 204. The data acquired by the data acquisition processor 206 is reconstructed using the image reconstruction processor 208.

The detector ring assembly 60 includes a central opening, in which an object or patient, such as patient 22 may be positioned using, for example, a motorized table 46 (shown in FIG. 1). The motorized table 46 may be aligned with the central axis of detector ring assembly 60. This motorized table 46 moves the patient 22 into the central opening of detector ring assembly 60 in response to one or more commands received from the operator workstation 204. A PET scanner controller 212, also referred to as the PET gantry controller, is provided (e.g., mounted) within PET system 200. The PET scanner controller 212 responds to the commands received from the operator workstation 204 through the communication link 210. Therefore, the scanning operation is controlled from the operator workstation 204 through PET scanner controller 212.

During operation, when a photon collides with a crystal 62 on a detector ring 60, it produces a scintillation event on the crystal. Each photomultiplier tube or photosensor produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 206.

The data acquisition processor 206 includes the event locator circuit 68, an acquisition CPU 70, and a coincidence detector 72. The data acquisition processor 206 periodically samples the signals produced by the acquisition circuits 66. The acquisition CPU 70 controls communications on a back-plane bus 74 and on the communication link 210. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other. Second, the line-of-response (LOR) formed by a straight line joining the two detectors that detect the coincidence event should pass through the field of view in the PET imaging system 200. Events that cannot be paired are discarded. Coincident event pairs are located and recorded as a coincidence data packet that is communicated through a physical communication link 78 to a sorter/histogrammer 80 in the image reconstruction processor 208.

The image reconstruction processor 208 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 208 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 210 through the image CPU 84. The image CPU 84 controls communication through communication bus 88. The array processor 86 receives data array 90 as an input and reconstructs images in the form of image array 92. Resulting image arrays 92 are then stored in memory module 82.

The images stored in the image array 92 are communicated by the image CPU 84 to the operator workstation 204. The operator workstation 204 includes a CPU 94, a display 96, and an input device 98. The CPU 94 connects to communication link 210 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system 200 and the positioning of the patient 22 for a scan. Similarly, the operator can control the display of the resulting image on the display 96 and can perform image-enhancement functions using programs executed by the workstation CPU 94.

As shown in FIG. 1, gantry 12 and gantry 13 may be positioned in proximity to each other. For example, gantry 12 and gantry 13 may be in face-sharing contact along at least portions of contacting surfaces of each gantry. Additionally or alternatively, gantry 12 and gantry 13 may be enclosed by a common outer housing. Gantry 12 and gantry 13 may be installed at the same medical facility and may be supported by the same ground surface (e.g., floor). Gantry 12 and gantry 13 may be positioned close enough to each other than a single table may be used to move a single patient though each bore, as shown.

Now referring collectively to FIGS. 3-4, a multi-modal imaging system 300 is shown. FIG. 3 shows a front view of the multi-modal imaging system 300, and FIG. 4 shows a side view of the multi-modal imaging system 300, as indicated by reference axes 399. System 300 includes a gantry 350 having a first bore 320 and a second gantry 351 having a second bore 330. In some embodiments, the gantry 350, first bore 320, gantry 351, and second bore 330 may be similar to the gantry 12, first bore 114, gantry 13, and second bore 116 shown by FIG. 1 and described above. The first bore 320 may be utilized during imaging of a subject (e.g., patient 22 shown by FIGS. 1-2 and described above) via a first modality unit 368 (shown by FIG. 4) of the multi-modal imaging system 300 (e.g., similar to first modality unit 100 shown by FIG. 1 and described above), and the second bore 330 may be utilized during imaging of the subject via a second modality unit 370 (shown by FIG. 4) of the multi-modal imaging system 300 (e.g., similar to second modality unit 102 shown by FIG. 1 and described above). The bores of the multi-modal imaging system 300 shown by FIGS. 3-4 are in a non-offset configuration (e.g., concentric configuration) such that the first bore 320 and second bore 330 share a same isocenter line 334. In some examples, the separate gantries 350, 351 may be enclosed in a common outer housing.

Gantry 350 and gantry 251 are shown supported by ground surface 310. Ground surface 310 may be a relatively flat, planar surface (e.g., a hospital floor). A height 302 of each gantry 350, 351 from the ground surface 310 extends parallel to the z-axis of reference axes 399, and a width 352 of each gantry 350, 351 extends parallel to the x-axis of reference axes 399, with the z-axis arranged perpendicular to the x-axis. The first bore 320 and second bore 330 each have a same diameter 314 and are centered at the gantries 350, 351 in the vertical direction (e.g., the direction of the z-axis of reference axes 399), with the isocenter line 334 centered at each of the first bore 320 and second bore 330. The first bore 320 and second bore 330 are aligned with each other such that each bore shares a same central axis (e.g., axis of rotation, similar to center of rotation 24 described above with reference to FIGS. 1-2). The isocenter line 334 of each of the first bore 320 and second bore 330 is positioned at a midpoint of the diameter 314 of the first bore 320 and second bore 330.

A top surface 360 of the first bore 320 is arranged at a same vertical position (e.g., a same height 304 relative to the ground surface 310) as a top surface 362 of the second bore 330. Axis 326 shown by FIG. 3 is arranged at the same height 304 as each of the top surface 360 of the first bore 320 and top surface 362 of the second bore 330. The top surface 360 of the first bore 320 is the portion of the first bore 320 positioned closest to upper surface 354 of gantry 350, and the top surface 362 of the second bore 330 is the portion of the second bore 330 positioned closest to upper surface 355 of gantry 351. Further, the height 304 between the axis 326 and the ground surface 310 in the vertical direction is greater than a height between the axis 326 and the upper surface 354 of the gantry 350.

A bottom surface 364 of the first bore 320 is arranged at a same vertical position (e.g., a same height 308) as a bottom surface 366 of the second bore 330. Axis 332 shown by FIG. 3 is arranged at the same height 308 relative to a lower surface 356 of the gantry 350 and the ground surface 310 as each of the bottom surface 364 of the first bore 320 and the bottom surface 366 of the second bore 330. The bottom surface 364 of the first bore 320 is the portion of the first bore 320 positioned closest to the lower surface 356 of the gantry 350 (with the lower surface 356 arranged opposite to the upper surface 350 and configured to be positioned adjacent to the ground surface 310), and the bottom surface 366 of the second bore 330 is the portion of the second bore 330 positioned closest to the lower surface 357 of the gantry 351.

Axis 328 is shown by FIG. 3 arranged parallel with the x-axis of reference axes 399 and intersecting the isocenter line 334 of the first bore 320 and second bore 330, with the isocenter line 334 positioned a height 306 from the lower surface 356 and ground surface 310 in the vertical direction. The top surface 360 of the first bore 320 and the top surface 362 of the second bore 330 (each shown by FIG. 4) are each a same height 322 from the axis 328 and isocenter line 334 in the vertical direction (e.g., the direction of the z-axis of reference axes 399). The bottom surface 364 of the first bore 320 and the bottom surface 366 of the second bore 330 (each shown by FIG. 4) are each a same height 324 from the axis 328 in the vertical direction, opposite to the top surface 360 and top surface 362. Further, the height 322 and the height 324 are the same amount of height, such that top surface 360 and top surface 362 are positioned away from the isocenter line 334 in the vertical direction by a same amount as the bottom surface 364 and bottom surface 366, with the top surfaces opposite to the bottom surfaces across the isocenter line 334. Height 322 and height 324, in combination, are a same amount (e.g., a same length) as the diameter 314.

The first bore 320 of the first modality unit 368 may be used to image a patient (e.g., patient 22 shown by FIG. 1) via at least a first imaging modality, and the second bore 330 of the second modality unit 370 may be used to image the patient via at least a different, second imaging modality. For example, the first bore 320 may be configured for imaging in a CT imaging modality, and the second bore 330 may be configured for imaging in a NM imaging modality. The first bore 320 and second bore 330 extend parallel to each other in the same axial direction, and during imaging of the patient, table 312 may move in the axial direction (e.g., the direction parallel to isocenter line 334) through one or each of the first bore 320 and second bore 330.

The table 312 (which may be similar to the table 46 described above with reference to FIGS. 1-2B), is shown positioned between the axis 326 and the axis 332 in the vertical direction. The position of the table 312 (e.g., the position of the table 312 in the direction of the z-axis of reference axes 399) is adjustable such that a center of a patient supported by the table 312 or other anatomical feature of the patient may be aligned with the isocenter line 334 during imaging of the patient. For example, aligning a smaller patient with the isocenter line 334 may include adjusting the table 312 to a higher, first position, and aligning a larger patient with the isocenter line 334 may include adjusting the table 312 to a lower, second position (e.g., due to the increased size of the larger patient relative to the smaller patient). Because the isocenter line 334 is vertically centered relative to each of the first bore 320 and second bore 330, adjusting the vertical position of the table 312 in order to center the patient at the isocenter line 334 may include adjusting the table 312 to a position vertically below the isocenter line 334 and the center of each of the first bore 320 and second bore 330. A width of the table 312 in the direction of the x-axis of reference axes 399 (and perpendicular to the vertical direction) is less than the diameter 314 of the first bore 320 and second bore 330 such that the table 314 may fit within each of the first bore 320 and second bore 330. In some embodiments, the width of the table 314 may be half (or less than half) of the diameter 314 of the bores.

Thus, the multi-modal imaging system 300 shown in FIGS. 3-4 may include two imaging bores of equal diameter (e.g., each 700 mm) and arranged in a concentric manner such that the isocenters of the two bores are aligned. By arranging the bores to be concentric and having aligned isocenters, the multi-modal imaging system 300 may enable images produced by both modalities to be easily aligned, and may enable the two modalities to have a common FOV that is as large as possible.

To accommodate a wide variety of patient sizes, reduce patient anxiety during scanning, etc., it may be desirable to increase the size of one or both of the imaging bores. For example, it may be desirable to increase the diameters of the bores to be 800 mm or larger. However, due to various constraints, increasing the size of the first bore may be more expensive or challenging than increasing the size of the second bore. As an example, when the first bore is a bore of a CT system, increasing the size of the first bore may result in the overall gantry size being increased (e.g., in a vertical direction) in order to accommodate the X-ray source, X-ray detectors, and associated componentry in the gantry surrounding the first bore. Increasing the overall size of the gantry may result in the CT system being too large (e.g., too high) to fit in some medical facilities. On the other hand, when the second bore is a bore of a PET or other nuclear medicine imaging system, it may be possible to increase the diameter of the second bore without having to increase the overall size of the associated gantry, as the PET or other NM imaging system may include fewer electronics/components than the CT system, which may allow a similar sized gantry to accommodate a larger bore.

Thus, according to embodiments disclosed herein, the diameter of the second bore may be increased relative to the diameter of the first bore. When the first bore and the second bore are included together in a hybrid/multi-modal imaging system, the two bores may be of different diameter. While such a configuration may still result in a smaller, first bore (and hence reduce some of the benefits of the increased diameter of the second bore, due to the patient still having to be imaged via the first bore, at least in some examples), the increased diameter of the second bore may still be beneficial. For example, if the second modality unit (e.g., nuclear medicine imaging system) is installed in a stand-alone imaging system (e.g., without the first modality unit), the increased bore size may more easily accommodate larger patients, while still allowing the second modality unit to be included in a multi-modal imaging system without requiring two separate and different systems to be manufactured. Said another way, an NM imaging system may be manufactured to have the increased bore diameter and the NM imaging system may be included as a stand-alone system or incorporated in a multi-modal system without increasing manufacturing costs. As another benefit, if the NM imaging system is included in the multi-modal imaging system but a patient is only being scanned by the NM imaging system and not the CT system, the increased bore size of the NM imaging system may accommodate larger patients and/or reduce patient anxiety, as the patient may not have to be moved through the first bore of the CT system.

When a multi-modal imaging system includes two bores of different diameter, and the bores are arranged concentrically as described above, the overall height of the multi-modal imaging system may be increased relative to the overall height of multi-modal imaging system 300 described above. While the NM imaging system may accommodate a larger bore without requiring a larger gantry, constraints on the configuration of the NM imaging system may dictate that a certain amount of headroom between the top of the bore of the NM imaging system and the top surface of the gantry/housing be present. Thus, simply aligning the isocenters as in FIGS. 3 and 4 may result in a multi-modal imaging system with undesirably high total height.

Thus, as shown in FIGS. 5-6 and described in more detail below, the second bore (e.g., of the NM imaging system) may be vertically offset from the first bore, with the top of the second bore aligned with the top of the first bore. Due to the larger diameter of the second bore, the bottom of the second bore may be lower (e.g., closer to the floor/ground) than the bottom of the first bore. Further, the isocenter of the second bore may be lower than the isocenter of the first bore.

This configuration may still allow for the FOVs of both imaging systems to be as large as possible, as the FOV of the first bore may fit within the FOV of the second bore. Further, image quality of images produced with the second imaging modality (e.g., the NM imaging system) may be increased for some patients, such as pediatric patients. This may be due to the lower isocenter of the second bore (relative to if the two bores were arranged concentrically). Some tables included in or used with the multi-modal imaging system may have a maximum table elevation that is below the isocenter of the first bore. When larger patients are imaged, this maximum table elevation constraint may not impact image quality, as the patient may be centered at the isocenter for each bore. However, for smaller patients, the maximum table elevation may be reached without the patient being centered at the isocenter of the first bore. If the bores were concentrically aligned, the patient would not be at the isocenter of either bore, even if the patient is only being imaged with the second imaging modality. However, by lowering the isocenter of the second bore as described herein, even smaller patients may be placed at the isocenter of the second bore, and even when the maximum table elevation is limited as described above.

Now referring collectively to FIGS. 5-6, a multi-modal imaging system 400 is shown according to an exemplary embodiment. FIG. 5 shows a front view of the multi-modal imaging system 400, and FIG. 6 shows a side view of the multi-modal imaging system 400, as indicated by reference axes 499. System 400 includes a first modality unit 490 having a gantry 450 including a first bore 414 and a second modality unit 492 having a gantry 451 having a second bore 420, with the first bore 414 and second bore 420 in an offset configuration relative to each other (e.g., a non-concentric configuration), as described further below. The first bore 414 may be configured to image via at least a first imaging modality, similar to the first bore 320 described above with reference to FIGS. 3-4, and the second bore 420 may be configured to image via at least a different, second imaging modality, similar to the second bore 330 described above with reference to FIGS. 3-4. In some embodiments, the first bore 414 may be configured for imaging via at least a CT imaging modality, and the second bore 420 may be configured for imaging via at least an NM imaging modality (e.g., PET). Although the first bore 414 and second bore 420 may be configured to image via the same imaging modalities as the first bore 320 and second bore 330, respectively, described above with reference to FIGS. 3-4, the first bore 414 and second bore 420 are positioned in a different relative arrangement (e.g., the offset configuration) such that the size (e.g., diameter) of each bore is different while maintaining a same size (e.g., height) of each gantry 450, 451 relative to the gantries 350, 351 shown by FIGS. 3-4.

The gantry 450 and gantry 451 each include several features similar to those described above with reference to the gantry 350 and gantry 351 shown by FIGS. 3-4. For example, the gantry 450 and gantry 451 are shown with the same height 302 and width 352 as the gantry 350. Although the bores of the gantries 450, 451 are sized differently relative to each other (e.g., the bores have different diameters), the offset configuration of the bores enables the height 302 of each gantry 450, 451 to be maintained (e.g., not increased to accommodate the differently sized bores), as described below.

The gantry 450 and gantry 451 are shown having the same height 302 and width 352 as the gantries 350, 351 for purposes of comparison of the bores of the system 400 in the offset configuration relative to the bores of the system 300 in the non-offset configuration (e.g., concentric configuration). However, the height and width of the gantries 450, 451 is not limiting. The gantry 450 includes the first bore 414 having a smaller, first diameter (shown as diameter 314 in FIG. 4) and gantry 451 includes the second bore 420 having a larger, second diameter (shown as diameter 402 in FIG. 4), with the first bore 414 and second bore 420 in the offset configuration as described herein. Although the height and width of the gantry 450 (and gantry 451) may be different than the height 302 and width 353 shown by FIG. 5 in some embodiments, the height and width of the gantry 450 (and gantry 451) is not greater than a height and width of conventional gantries that include bores of a same diameter in the non-offset configuration. As one example, a conventional imaging system may include two bores in the concentric configuration, with each bore having the smaller, first diameter 314, and with each gantry having the width 352 and height 302. Although the gantry 451 includes the second bore having the larger, second diameter 402, the width and height of the gantry 451 are maintained at the width 352 and height 302, respectively. As another example, a conventional imaging system may include two bores in the concentric configuration, with each bore having a same, given diameter that is different from each of the diameter 314 and diameter 402, and with the conventional system having gantries each having a given width and height that may be different than the width 352 and height 302. A system configured as described according to the present disclosure with a first bore and second bore in the offset configuration (e.g., similar to gantry 450) may have the same given gantry width and height due to the offset configuration of the bores, despite the second bore being larger than the first bore having the given diameter. As such, the offset configuration provides a reduction in size of the gantries of the present disclosure relative to gantries that include bores having different diameters in the non-offset configuration.

With regard to the system 400 shown by FIGS. 5-6, the diameter 314 of the first bore 414 may be the same as the diameter 314 of each of the first bore 320 and second bore 330 shown by FIGS. 3-4, at least in some embodiments. However, diameter 402 of the second bore 420 is different (e.g., larger) than the diameter 314 of the first bore 414. The larger diameter 402 of the second bore 420 may provide increased space to accommodate larger patients during imaging (e.g., imaging via NM imaging modalities). A vertical position of the first bore 414 relative to the gantry 450 may be the same as the vertical position of the first bore 320 and second bore 330 relative to the gantry 350 shown by FIGS. 3-4, at least in some embodiments.

Axis 408 shown by FIG. 5 is arranged at the same height 304 as each of the top surface 470 of the first bore 414 and top surface 472 of the second bore 420 (with the top surface 470 and top surface 472 each shown by FIG. 6). The top surface 470 of the first bore 414 is the portion of the first bore 414 positioned closest to upper surface 454 of gantry 450, and the top surface 472 of the second bore 420 is the portion of the second bore 420 positioned closest to upper surface 455 of gantry 451. Further, the height 304 between the axis 408 and the ground surface 310 in the vertical direction is greater than a height between the axis 408 and the upper surface 454 of the gantry 450.

Although the top surface 470 of the first bore 414 and the top surface 472 of the second bore 420 are arranged at the same vertical position, a bottom surface 474 of the first bore 414 and a bottom surface 476 of the second bore 420 are not arranged at a same vertical position. Due to the increased diameter 402 of the second bore 420 relative to the diameter 314 of the first bore 414 and the alignment of the top surface 470 with the top surface 472, a bottom surface 474 of the first bore 414 is arranged at a larger, first height 308 from lower surface 456 of the gantry 450 adjacent to ground surface 310 while a bottom surface 476 of the second bore 420 is arranged at a smaller, second height 460 from the lower surface 457 of gantry 451. Axis 416 shown by FIG. 5 extends parallel with the x-axis of reference axes 499 and is arranged at the bottom surface 474 of first bore 474, with height 308 extending between axis 416 and the lower surface 356 of gantry 450 in the vertical direction (e.g., the direction of the z-axis of reference axes 499, perpendicular to the x-axis). Axis 418 shown by FIG. 5 extends parallel with the x-axis of reference axes 499 and is arranged at the bottom surface 476 of second bore 420, with height 460 extending between axis 418 and the lower surface 357 of gantry 451 in the vertical direction. The bottom surface 474 of the first bore 414 is the portion of the first bore 414 positioned closest to the lower surface 456 of the gantry 450 (with the lower surface 456 arranged opposite to the upper surface 450 and configured to be positioned adjacent to the ground surface 310), and the bottom surface 476 of the second bore 420 is the portion of the second bore 420 positioned closest to the lower surface 457 of the gantry 451. In this configuration, the bottom surface 474 of the first bore 414 is offset from the bottom surface 476 of the second bore 420 by height 422 in the vertical direction.

Axis 410 is shown by FIG. 5 arranged parallel with the x-axis of reference axes 499 and intersecting isocenter line 404 of the first bore 414, with the isocenter line 404 arranged at height 306 from the lower surface 456 and ground surface 310 in the vertical direction (e.g., the same height 306 of isocenter line 334 from lower surface 356 as shown by FIG. 3). The top surface 470 of the first bore 414 and the top surface 472 of the second bore 420 (each shown by FIG. 6) are each a same height 408 from the axis 410 and isocenter line 404 in the vertical direction (e.g., the direction of the z-axis of reference axes 499). The bottom surface 474 of the first bore 414 is arranged away from the axis 328 by height 482 in the vertical direction, opposite to the top surface 470. Further, the height 480 and the height 482 are the same amount of height. In this configuration, the top surface 470 and top surface 472 are each positioned away from the isocenter line 404 in the vertical direction by a same amount. However, while the bottom surface 474 is positioned away from the isocenter line 404 by height 482 in the vertical direction, the bottom surface 476 is positioned away from the isocenter line 404 in the vertical direction by a greater height (e.g., a combination of height 482 and height 422).

Due to the larger diameter 402 of the second bore 420 relative to the smaller diameter 314 of the first bore 414, along with the top surface 470 of the first bore 414 being arranged in the same vertical position as the top surface 472 of the second bore 420, an isocenter line 406 of the second bore 420 is at a vertically lower position than the isocenter line 404 of the first bore 414. FIG. 5 shows axis 412 arranged parallel with the x-axis of reference axes 499 and intersecting the isocenter line 406 of the second bore 414. A height 424 in the vertical direction between the lower surface 457 of the gantry 451 and the isocenter line 406 (and axis 412) is less than the height 306 in the vertical direction between the lower surface 456 of the gantry 450 and the isocenter line 404 (and axis 410). In this configuration, the isocenter line 406 of the second bore 420 is offset from the isocenter line 404 of the first bore 414 in the vertical direction by height 458 and is positioned closer to the lower surface 457 of the gantry 451 than the isocenter line 404 of the first bore 414.

In the offset configuration of the first bore 414 and second bore 420 as described above, the second bore 420 is provided a larger diameter (e.g., diameter 402) relative to the smaller diameter of the first bore 414 (e.g., diameter 314) while maintaining the width 352 and height 302 of the gantries 450, 451 (e.g., not increasing the width 352 or the height 302 of the gantry 451 to accommodate the larger diameter 402 of the second bore 420). Further, the isocenter line 406 of the second bore 420 is positioned closer to the lower surface 457 of the gantry 451, providing a lower elevation (e.g., height) of the table 312 to center a subject (e.g., patient 22 shown by FIG. 1 and described above) at the isocenter line 406.

For example, similar to the example described above with reference to table 46 shown by FIGS. 1-2, the table 312 (which may be similar to the table 46) may be configured with a set maximum vertical extension amount (e.g., a maximum height to which the table may be adjusted). Systems that include bores of different sizes (e.g., a first bore having a smaller diameter and a second bore having a larger diameter configured for imaging larger patients) with the bores in the non-offset configuration (e.g., arranged concentrically relative to each other) may not be well suited for imaging smaller patients (e.g., patients having a thickness of approximately 20 centimeters, such as pediatric patients) due to the maximum vertical extension amount of the table being less than an amount of vertical extension for positioning the patient at the isocenter line of the larger bore. However, by arranging the first bore 414 and second bore 420 in the offset configuration as described herein (and as shown by FIGS. 5-6), the isocenter line 406 of the second bore 420 is lowered (e.g., positioned closer to the lower surface 457), and a larger variety of patients (e.g., patients having different sizes) may be imaged while supported by the table 312. In some examples, the maximum vertical extension amount of the table 312 may be height 358 (with height 358 extending in the vertical direction between ground surface 310 and a vertically lowest portion of support surface 496 of table 312, where support surface 496 is configured to be in face-sharing contact with the subject to be imaged). In particular, tables having a maximum vertical extension amount suitable for use with systems having bores in the non-offset configuration (e.g., concentric configuration) may be used to support patients for imaging via the system 400 due to the lower isocenter line 406 (e.g., as compared imaging via a bore having the diameter 402 with an isocenter line at the same vertical position as isocenter line 404).

Further, although the second bore 420 has increased diameter 402 relative to the diameter 404 of first bore 414, the offset configuration of the bores increases an overlap of the field of view (FOV) of the bores and aligns the FOV of each bore (where the FOV of the bores refers to the FOV of detectors of the bores used for imaging the patient, with the FOV of the detectors of a given modality unit, such as second modality unit 492, increasing as the size of the bore of the given modality unit, such as second bore 420, increases). Due to the larger size of the second bore 420, the FOV of the second bore 420 may be larger than the FOV of the first bore 414. During imaging of a patient via the first bore 414, a first amount of the body of the patient may be imaged (e.g., with the first amount corresponding to the amount of the body of the patient positioned in the FOV of the first bore 414). Because the FOV of the second bore 420 is larger than the FOV of the first bore 414, during imaging of the patient via the second bore 420, at least the first amount of the body of the patient may be imaged (although the FOV of the second bore 420 may provide imaging of additional portions of the body of the patient due to the increased size relative to the FOV of the first bore 414). As a result, the configuration of the bores described herein reduces or eliminates losses in imaging quality resulting from differences in FOV size of the bores.

Additionally, because the top surfaces of the bores (e.g., top surface 470 of first bore 414 and top surface 472 of second bore 420) are arranged at the same vertical position in the offset configuration, the FOV of each bore has a same point of alignment (e.g., reference point). For example, the system 400 may generate a first image of a patient by imaging the patient via the first bore 414, and the system 400 may generate a second image of the patient by imaging the patient via the second bore 420. Due to the alignment of the FOVs of each bore (e.g., the axial alignment of the FOVs along an axis at the same vertical position as the top surfaces of the bores), the system 400 may more easily align each image and/or generate a superposition of each of the first image and second image for viewing by an operator of the system 400 (e.g., a clinician, radiologist, etc.). Further, the system 400 may more easily (e.g., with less image processing) identify and/or label anatomical features of the body of the patient that have been imaged by both of the first bore 414 and second bore 420. (e.g., portions of the body positioned in both of the FOV of the first bore 414 and the FOV of the second bore 420).

In one non-limiting example, the diameter of the first bore 414 may be 700 mm and the diameter of the second bore 420 may be 800 mm. The height 496 may be 1030 mm and the height 306 may be 1080 mm, resulting in height 422 being 50 mm. The maximum table elevation may be 1003 mm. Thus, at the maximum table elevation, the table (e.g., the top surface of the table) may be 27 mm below the isocenter of the second bore and 77 mm below the isocenter of the first bore.

In some examples, the separate gantries 450, 451 may be enclosed in a common outer housing. Further, while FIGS. 1-6 have been described above with the table positioned to first move through the first bore of the first modality unit before moving through the second bore of the second modality unit, with the first modality unit being a CT system and the second modality unit being a PET system, it should be understood that in some examples, the table may be positioned on an opposite side of the imaging system such that the table first moves through the second bore of the second modality unit before moving through the first bore of the first modality unit.

As shown in FIG. 6, gantry 450 and gantry 451 may be positioned in proximity to each other. For example, gantry 450 and gantry 451 may be in face-sharing contact along at least portions of contacting surfaces of each gantry. Additionally or alternatively, gantry 450 and gantry 451 may be enclosed by a common outer housing. Gantry 450 and gantry 451 may be installed at the same medical facility and may be supported by the same ground surface (e.g., floor). Gantry 450 and gantry 451 may be positioned close enough to each other than a single table may be used to move a single patient though each bore, as shown.

Figure 7:
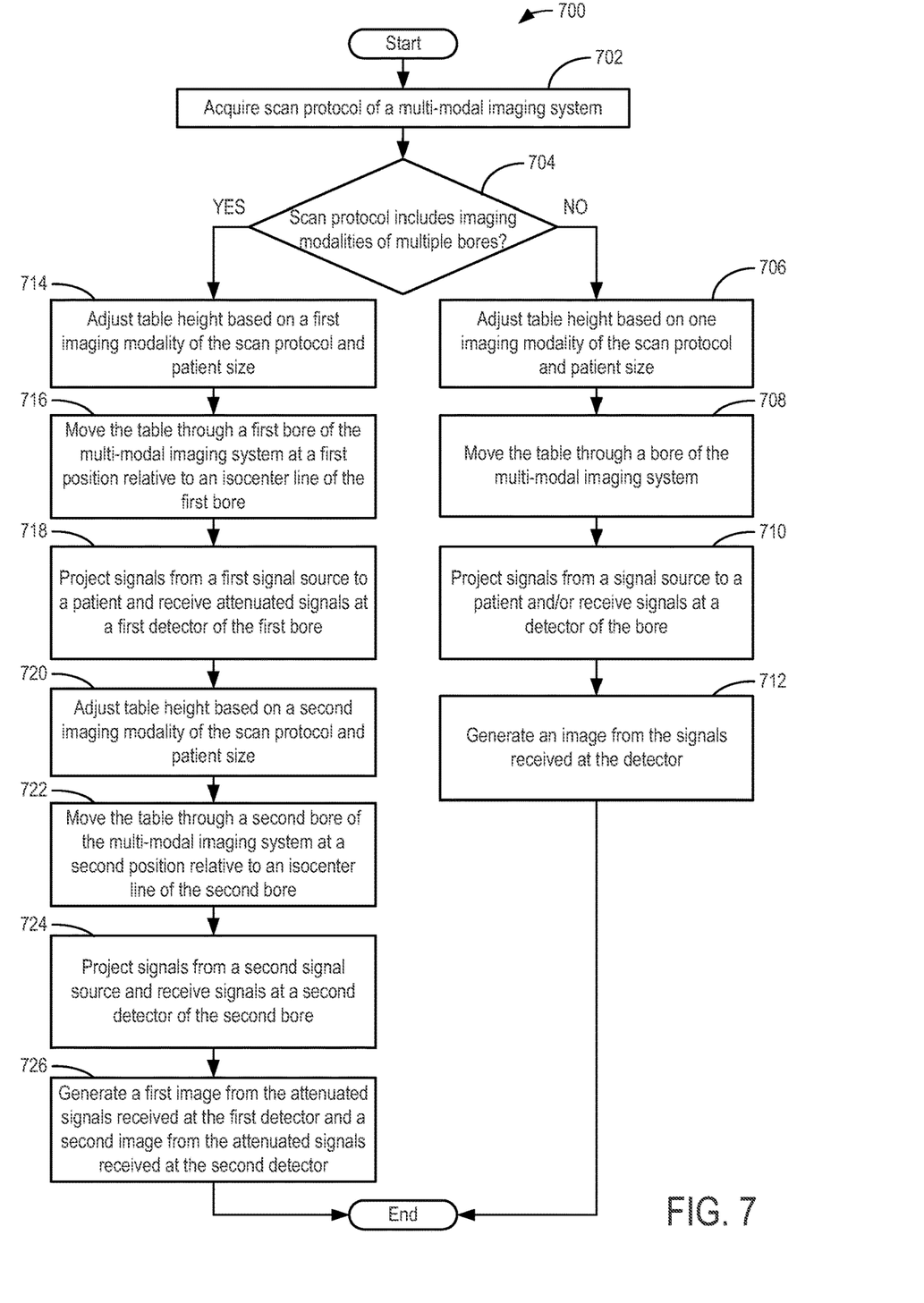
FIG. 7 shows a flowchart illustrating a method for imaging a subject via a multi-modal imaging system, according to an exemplary embodiment.

Now referring to FIG. 7, a flowchart illustrating a method 700 for imaging a subject via a multi-modal imaging system is shown. The multi-modal imaging system includes a first bore (e.g., similar to first bore 414 described above with reference to FIGS. 5-6) configured for imaging of a subject (e.g., patient 22 shown by FIGS. 1-2 and described above) via at least a first imaging modality, and a second bore (e.g., similar to second bore 420 described above with reference to FIGS. 5-6) configured for imaging the subject via at least a second imaging modality. In some examples, the multi-modal imaging system may be the multi-modal imaging system 400 shown by FIGS. 5-6 and described above.

At 702, a scan protocol of a multi-modal imaging system is acquired. Acquiring the scan protocol may include receiving a selection of the scan protocol from an operator of the multi-modal imaging system (e.g., a clinician) via a user interface of the multi-modal imaging system. In some examples, the scan protocol may be acquired by a computer configured to receive commands and scanning parameters from an operator via a console that includes a user input device, with the computer and console being similar to those described above with reference to FIG. 2 (e.g., computer 36 and operator console 40, respectively). The scan protocol may include a selection of one or more imaging modalities of the multi-modal imaging system. For example, the scan protocol may include a selection to scan a subject (e.g., patient 22 described above with reference to FIGS. 1-2) via both of a first imaging modality of the first bore of the multi-modal imaging system (e.g., CT) and a second imaging modality of the second bore of the multi-modal imaging system (e.g., PET). As another example, the scan protocol may include a selection to scan the subject via only a single imaging modality, with the single imaging modality being an imaging modality of either the first bore or second bore (e.g., CT or an NM imaging modality).

At 704, a determination is made of whether the scan protocol includes imaging modalities of multiple bores. In one example, the determination may be made by the computer based on the input of the operator of the multi-modal imaging system (e.g., the selection of the scan protocol by the operator). As described above, the multi-modal imaging system includes the first bore configured for imaging via at least the first imaging modality and the second bore configured for imaging via at least the second imaging modality. The determination at 704 refers to determining whether the scan protocol includes imaging via both the first imaging modality and the second imaging modality, where the first imaging modality is any imaging modality utilized during imaging via the first bore and the second imaging modality is any imaging modality utilized during imaging via the second bore. As one example, the first bore may be configured for imaging via the CT imaging modality and not the PET imaging modality, while the second bore may be configured for imaging via the PET imaging modality and not the CT imaging modality. The determination at 704 may include determining whether the scan protocol includes imaging via both of the CT imaging modality and the PET imaging modality. Although CT and PET imaging modalities are described herein as example imaging modalities of the first bore and second bore, respectively, the example imaging modalities are not limiting.

If it is determined that the scan protocol does not include multiple imaging modalities at 704, table height is adjusted based on the one imaging modality of the scan protocol and patient size at 706. The one imaging modality may be an imaging modality of either the first bore or the second bore (e.g., not an imaging modality of both the first bore and second bore). Imaging via the one imaging modality may include centering the patient at an isocenter line of the associated bore (e.g., the first bore or second bore) utilized for imaging via the one imaging modality.

As one example, it may be determined at 704 that the one imaging modality of the scan protocol is an imaging modality of the first bore and not the second bore (e.g., the CT imaging modality, where the first bore is configured for imaging via the CT imaging modality and the second bore is not configured for imaging via the CT imaging modality). The first bore is configured with a first diameter and a first isocenter line (e.g., diameter 314 and isocenter line 404, respectively, shown by FIG. 5 and described above), and the body of the patient has a given thickness in the vertical direction of the first bore (e.g., the direction of the z-axis of reference axes 499 shown by FIG. 5 and described above). Adjusting the table height at 706 may include, responsive to the determination that the scan protocol includes the CT imaging modality (e.g., the imaging modality of the first bore), centering the thickness of the patient at the first isocenter line of the first bore by increasing and/or decreasing the height of the table (e.g., the amount of extension of the table in the vertical direction).

As another example, it may be determined at 704 that the one imaging modality of the scan protocol is an imaging modality of the second bore and not the first bore (e.g., the PET imaging modality, where the second bore is configured for imaging via the PET imaging modality and the first bore is not configured for imaging via the PET imaging modality). The second bore is configured with a different, second diameter and a different, second isocenter line (e.g., diameter 402 and isocenter line 406, respectively, shown by FIG. 5 and described above), and the body of the patient has a given thickness in the vertical direction of the second bore (e.g., the direction of the z-axis of reference axes 499 shown by FIG. 5 and described above). Adjusting the table height at 706 may include, responsive to the determination that the scan protocol includes the PET imaging modality (e.g., the imaging modality of the second bore), centering the thickness of the patient at the second isocenter line of the second bore by increasing and/or decreasing the height of the table (e.g., the amount of extension of the table in the vertical direction).

At 708, the table is moved through a bore of the multi-modal imaging system. Moving the table through the bore includes adjusting the position of the table in an axial direction of the bore (e.g., the direction of the associated isocenter line of the bore). As described above, the bore may be either the first bore or the second bore based on the one imaging modality included by the scan protocol (e.g., the bore may be the first bore during conditions in which the scan protocol includes imaging via the CT imaging modality, or the bore may be the second bore during conditions in which the scan protocol includes imaging via the PET imaging modality).

At 710, signals are projected from a signal source to the patient and/or signals are received at a detector of the bore. As one example, during conditions in which the one imaging modality of the scan protocol is the CT imaging modality of the first bore, signals may be projected from an X-ray source of the first bore (e.g., X-ray source 14 configured to project a beam of X-rays 16, as described above with reference to FIGS. 1-2), and attenuated signals (e.g., attenuated X-rays) may be received at a detector of the first bore (e.g., detector array 18), where the attenuated X-rays correspond to X-rays from the signal source that have passed through the body of the patient. As another example, during conditions in which the one imaging modality of the scan protocol is the PET imaging modality of the second bore, signals (e.g., photons) may be projected from a signal source within the body of the patient (e.g., a radiopharmaceutical agent injected into the patient or ingested by the patient), and resultant signals may be received at a detector of the second bore (e.g., second detector 60 shown by FIG. 1 and described above).

At 712, an image is generated from the signals received at the detector. Generating the image from the signals may include sampling analog data from the detector via a data acquisition system (e.g., DAS 32 described above with reference to FIG. 2) and converting the analog data to digital signals for subsequent processing. An image re-constructor (e.g., image re-constructor 34 described above) receives the sampled and digitized signal data from the data acquisition system and performs high-speed image reconstruction. The reconstructed image is applied as an input to a computer which stores the image in a storage device (e.g., computer 36 and storage device 36, respectively, described above). An associated visual display unit (e.g., visual display unit 42 described above) may display the reconstructed image to the operator for observation (e.g., patient diagnosis and/or analysis).

Returning to 704, if it is determined that the scan protocol includes multiple imaging modalities at 704, table height is adjusted based on a first imaging modality of the scan protocol and patient size at 714. For example, at 704, the determination may be made by the computer based on the input of the operator of the multi-modal imaging system (e.g., the selection of the scan protocol by the operator). As described above, multiple imaging modalities refers to imaging via both the first imaging modality and the second imaging modality, where the first imaging modality is any imaging modality utilized during imaging via the first bore (e.g., the CT imaging modality) and the second imaging modality is any imaging modality utilized during imaging via the second bore (e.g., the PET imaging modality or other NM imaging modality). At 714, the table height is adjusted based on the first imaging modality. Imaging via the first imaging modality may include centering the patient at the first isocenter line of the first bore, where the first isocenter line is offset from the second isocenter line of the second bore.

As described above, the first bore is configured with the first diameter and the first isocenter line (e.g., diameter 314 and isocenter line 404, respectively, shown by FIG. 5 and described above), and the body of the patient has thickness in the vertical direction of the first bore (e.g., the direction of the z-axis of reference axes 499 shown by FIG. 5 and described above). Adjusting the table height at 714 may include, responsive to the determination that the scan protocol includes the first imaging modality of the first bore and the second imaging modality of the second bore, centering the thickness of the patient at the first isocenter line of the first bore by increasing and/or decreasing the height of the table (e.g., the amount of extension of the table in the vertical direction).

At 716, the table is moved through a first bore of the multi-modal imaging system at a first position relative to an isocenter line of the first bore. Moving the table through the first bore includes adjusting the position of the table in an axial direction of the first bore (e.g., the direction of the first isocenter line of the first bore).

At 718, signals are projected from a first signal source to a patient and attenuated signals are received at a first detector of the first bore. As one example, the signals may be X-rays projected from the first signal source of the first bore (e.g., first signal source 14 configured to project a beam of X-rays 16, as described above with reference to FIGS. 1-2), and the attenuated signals (e.g., attenuated X-rays) may be received at a detector of the first bore (e.g., detector array 18), where the attenuated X-rays correspond to X-rays from the signal source that have passed through the body of the patient.

At 720, table height is adjusted based on a second imaging modality of the scan protocol and patient size. As described above, the second bore is configured with the second diameter and the second isocenter line (e.g., diameter 402 and isocenter line 406, respectively, shown by FIG. 5 and described above), and the body of the patient has thickness in the vertical direction of the second bore (e.g., the direction of the z-axis of reference axes 499 shown by FIG. 5 and described above). Adjusting the table height at 720 may include centering the thickness of the patient at the second isocenter line of the second bore by decreasing the height of the table (e.g., lowering the amount of extension of the table in the vertical direction).

At 722, the table is moved through a second bore of the multi-modal imaging system at a second position relative to an isocenter line of the second bore. Moving the table through the second bore includes adjusting the position of the table in an axial direction of the second bore (e.g., the direction of the second isocenter line of the second bore).

At 724, signals are projected from a second signal source and signals are received at a second detector of the second bore. As one example, signals (e.g., photons) may be projected from a signal source within the body of the patient (e.g., a radiopharmaceutical agent injected into the patient or ingested by the patient), and the projected signals may be received at a detector of the second bore (e.g., second detector 60 shown by FIG. 1 and described above).

At 726, a first image is generated from the attenuated signals received at the first detector and a second image is generated from the signals received at the second detector. For example, the first image may be an image generated by the CT imaging modality and may comprise a set of views of anatomical structures of the patient (e.g., bones of the patient), while the second image may be an image generated by the PET imaging modality and may comprise a set of views showing a metabolic pathway including one or more organs and/or vessels of the patient. In some examples, at 726, the computer may generate a combined image including data acquired from both imaging modalities (e.g., a combined CT/PET image).

Although imaging the patient via the first bore and second bore is described above, with imaging via the first bore occurring prior to imaging via the second bore, in other examples the patient may first be imaged via the second bore and then imaged via the first bore. For example, the table may be adjusted to center the patient at the second isocenter line for imaging the patient at the second bore prior to adjusting the table to center the patient at the first isocenter line for imaging the patient at the first bore (e.g., during conditions in which NM imaging is performed first, and CT imaging is performed second).

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Also as used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
a first gantry including a first bore having a smaller, first diameter and a smaller, first imaging field of view and a second gantry including a second bore having a larger, second diameter and a larger, second imaging field of view, with each of the first bore and the second bore shaped to encircle a subject to be imaged by the medical imaging system, with the first bore having a first isocenter line, and with the second bore having a second isocenter line shifted vertically from the first isocenter line away from a top surface of the second bore, and with a top surface of the first bore and the top surface of the second bore each spaced apart from the first isocenter line by a smaller, first length and spaced apart from the second isocenter line by a larger, second length.

2. The medical imaging system of claim 1, wherein the first bore is configured for imaging via a first imaging modality, and the second bore is configured for imaging via a different, second imaging modality.

3. The medical imaging system of claim 2, wherein the first imaging modality is computerized tomography (CT), and the second imaging modality is a nuclear medicine (NM) imaging modality.

4. The medical imaging system of claim 1, wherein the first gantry and the second gantry are positioned in face-sharing contact and/or are positioned in a common housing.

5. The medical imaging system of claim 4, wherein the first isocenter line and the second isocenter line are aligned in a vertical direction extending from an upper surface of the first gantry to a lower surface of the first gantry, the lower surface adjacent to a ground surface on which the first gantry sits.

6. The medical imaging system of claim 1, wherein the first isocenter line is arranged above the second isocenter line in a vertical direction.

7. The medical imaging system of claim 1, wherein the top surface of the first bore is aligned with the top surface of the second bore.

8. The medical imaging system of claim 1, wherein the first imaging field of view and the second imaging field of view are axially aligned along the top surface of the first bore and the top surface of the second bore.

9. The medical imaging system of claim 1, wherein a difference between the first diameter and the second diameter is equal to a length in a vertical direction between a bottom surface of the first bore and a bottom surface of the second bore.

10. A method, comprising:
acquiring a scan protocol of a multi-modal imaging system including a first bore and a second bore in a vertically offset configuration; and
first, adjusting a height of a table based on a first imaging modality of the scan protocol and a patient size, and moving the table through the first bore at a first vertical position along a first isocenter line of the first bore;
then, adjusting the height of the table based on a second imaging modality of the scan protocol and the patient size, and moving the table through the second bore at a second vertical position along a second isocenter line of the second bore.

11. The method of claim 10, wherein moving the table through the first bore at the first vertical position includes projecting signals from a first signal source and receiving corresponding signals at a first detector of the first bore, and wherein moving the table through the second bore at the second vertical position includes projecting signals from a second signal source and receiving corresponding signals at a second detector of the second bore.

12. The method of claim 11, wherein projecting signals from the first signal source and receiving corresponding signals at the first detector includes projecting X-rays from the first signal source and receiving attenuated X-rays at the first detector, and wherein projecting signals from the second signal source and receiving corresponding signals at the second detector includes projecting gamma radiation from within a body of the patient via a radiopharmaceutical and receiving the gamma radiation at the second detector.

13. The method of claim 11, wherein projecting signals from the first signal source and receiving corresponding signals at the first detector includes projecting gamma radiation from within a body of the patient via a radiopharmaceutical and receiving the gamma radiation at the first detector, and wherein projecting signals from the second signal source and receiving corresponding signals at the second detector includes projecting X-rays from the second signal source and receiving attenuated X-rays at the second detector.

14. The method of claim 11, further comprising generating a first image from the corresponding signals received at the first detector and a second image from the corresponding signals received at the second detector.

15. A medical imaging system, comprising:
a first gantry including a first bore having a larger, first diameter and extending from a front of the first gantry to a rear of the first gantry, and a second gantry including a second bore having a smaller, second diameter and extending from a front of the second gantry to a rear of the second gantry, where the first bore opens to the second bore at the rear of the first gantry and the front of the second gantry;
a first detector arranged at the first bore, where the first detector is configured to detect radiation generated via a nuclear medicine (NM) imaging modality;
a second detector arranged at the second bore, where the second detector is configured to detect radiation generated via a computerized tomography (CT) imaging modality; and
wherein the first bore is offset from the second bore in a vertical direction toward a lower surface of the first gantry adjacent to a ground surface on which the first gantry and the second gantry sit.

16. The medical imaging system of claim 15, wherein the first bore and second bore extend in a same axial direction.

17. The medical imaging system of claim 15, wherein a top surface of the first bore is arranged at a same position in the vertical direction as a top surface of the second bore relative to the ground surface on which the first gantry and the second gantry sit, and wherein a first isocenter line of the first bore is spaced apart from a second isocenter line of the second bore in the vertical direction toward the lower surface.

18. The medical imaging system of claim 17, further comprising a table configured to support a patient, where a height of the table is adjustable to center a thickness of the patient at the first isocenter line and second isocenter line.

19. The medical imaging system of claim 17, wherein a bottom surface of the first bore is positioned below a bottom surface of the second bore in the vertical direction.

20. The medical imaging system of claim 15, wherein a length of overlap of a field of view of the first detector with a field of view of the second detector in the vertical direction is equal to a difference between the first diameter and the second diameter.

* * * * *